US011918629B2

(12) United States Patent
Nur et al.

(10) Patent No.: US 11,918,629 B2
(45) Date of Patent: Mar. 5, 2024

(54) LOW CONCENTRATED PROTEIN COMPOSITIONS FOR PREVENTING TISSUE ADHESION

(71) Applicant: Omrix Biopharmaceuticals Ltd., Rehovot (IL)

(72) Inventors: Israel Nur, Nes-Ziona (IL); Elena Grimberg, Rehovot (IL); Itai Podoler, Rehovot (IL); Inbar Gahali-Sass, Mazkeret Batya (IL); Erez Ilan, Kibbutz Netzer Sereni (IL); Ronen Eavri, Binyamina (IL)

(73) Assignee: Omrix Biopharmaceuticals Ltd., Rehovot (IL)

( * ) Notice: Subject to any disclaimer, the term of this patent is extended or adjusted under 35 U.S.C. 154(b) by 0 days.

(21) Appl. No.: 16/710,541

(22) Filed: Dec. 11, 2019

(65) Prior Publication Data

US 2020/0188489 A1 Jun. 18, 2020

Related U.S. Application Data

(60) Provisional application No. 62/778,331, filed on Dec. 12, 2018.

(30) Foreign Application Priority Data

Dec. 12, 2018 (IL) .......................................... 263679

(51) Int. Cl.
| | | |
|---|---|---|
| *A61K 38/00* | (2006.01) | |
| *A61K 9/08* | (2006.01) | |
| *A61K 33/06* | (2006.01) | |
| *A61K 38/36* | (2006.01) | |
| *A61K 38/37* | (2006.01) | |
| *A61K 38/38* | (2006.01) | |
| *A61K 38/48* | (2006.01) | |
| *A61P 7/04* | (2006.01) | |
| *A61P 41/00* | (2006.01) | |

(52) U.S. Cl.
CPC .............. *A61K 38/363* (2013.01); *A61K 9/08* (2013.01); *A61K 33/06* (2013.01); *A61K 38/366* (2013.01); *A61K 38/37* (2013.01); *A61K 38/38* (2013.01); *A61K 38/4833* (2013.01); *A61P 7/04* (2018.01); *A61P 41/00* (2018.01); *C12Y 304/21005* (2013.01)

(58) Field of Classification Search
CPC .... A61K 33/06; A61K 38/363; A61K 38/366; A61K 38/38; A61K 38/00; A61K 38/37; A61K 38/4833; A61K 9/08; A61P 41/00; A61L 2400/06; A61L 31/046; A61L 31/145; C12Y 304/21005

See application file for complete search history.

(56) References Cited

U.S. PATENT DOCUMENTS

| | | | |
|---|---|---|---|
| 2,390,074 A | 12/1945 | Cohn | |
| 4,297,344 A | 10/1981 | Schwinn et al. | |
| 4,455,300 A | 6/1984 | Wallace et al. | |
| 5,989,215 A * | 11/1999 | Delmotte ............. | A61L 31/046 604/82 |
| 6,121,232 A | 9/2000 | Nur et al. | |
| 6,613,325 B1 | 9/2003 | Amery et al. | |
| 6,965,014 B1 | 11/2005 | Delmotte | |
| 9,328,338 B2 | 5/2016 | Meidler et al. | |
| 2002/0001584 A1 | 1/2002 | Metzner et al. | |
| 2010/0203033 A1* | 8/2010 | Nur ...................... | A61L 24/106 424/94.63 |
| 2014/0205636 A1* | 7/2014 | Khatri ................. | A61L 24/0094 424/94.64 |
| 2016/0317700 A1* | 11/2016 | MacPhee .......... | A61F 13/00068 |

FOREIGN PATENT DOCUMENTS

| | | | |
|---|---|---|---|
| EP | 0534178 | 4/2001 | |
| EP | 1837039 B1 | 8/2001 | |
| EP | 1695724 A1 * | 8/2006 | ............. A61L 31/14 |
| EP | 1695724 A1 | 8/2006 | |
| EP | 1390485 | 10/2006 | |
| EP | 2011524 A1 | 1/2009 | |
| WO | WO 1993005822 A1 * | 4/1993 | |

(Continued)

OTHER PUBLICATIONS

Dhillon Sohita. Fibrin Sealant. Drugs 2011; 71 (14): 1893-1915 (Year: 2011).*

Buchta et al. Biochemical characterization of autologous fibrin sealants produced by CryoSeal® and Vivostat® in comparison to the homologous fibrin sealant product Tissucol/Tisseel. iomaterials 26 (2005) 6233-6241 (Year: 2005).*

C.W. Dunnett, Dunnett's Test New Tables for Multiple Comparisons with a Control, Biometrics, 1964, pp. 482-491, vol. 20.

(Continued)

*Primary Examiner* — Aradhana Sasan
*Assistant Examiner* — Mercy H Sabila
(74) *Attorney, Agent, or Firm* — David R. Crichton

(57) ABSTRACT

Provided herein are kits comprised of a first container including a solution of fibrinogen-containing component that includes fibrinogen at a concentration range of about 5 mg/ml to about 30 mg/ml, and having a total protein concentration range of about 15 mg/ml to about 40 mg/ml; and a second container that includes a solution of thrombin-containing component. Further provided are mixtures comprised of fibrinogen and thrombin, calcium ions, and albumin, the mixture being comprised of total protein in a range of about 2.5 mg/ml to about 30 mg/ml, fibrinogen in a range of about 50% to about 80% of total protein, and albumin in a range of more than 0.65 mg/ml to about 3 mg/ml. Further provided herein are methods for preventing or reducing tissue adhesion, and hydrogel materials made of fibrin.

11 Claims, No Drawings

(56) References Cited

FOREIGN PATENT DOCUMENTS

| WO | 9622115 A1 | 7/1996 | | |
| WO | WO-9622115 A1 | * 7/1996 | ........... | A61L 27/225 |
| WO | 98/033533 | 8/1998 | | |
| WO | 98/055140 A1 | 12/1998 | | |
| WO | WO-9855140 A1 | * 12/1998 | ........... | A61L 24/106 |
| WO | 2013001524 A1 | 1/2013 | | |
| WO | WO-2017098493 A1 | * 6/2017 | ........... | A61K 38/363 |

OTHER PUBLICATIONS

Cohn, et al., A System for the Separation of the Components of Human Blood: Quantitative Procedures for the Separation of the Protein Components of Human Plasma, Separation of Protein Components of Human Plasma, Jan. 1950, pp. 465-474, vol. 72.

Cohn, et al., Preparation and Properties of Serum and Plasma Proteins. IV A System for the Separation in Fractions of the Protein and Lipoproten Components of Biological Tissues and Fluids, Journal American Chemical Society, 1945, pp. 459-475, vol. 68.

Guerrier, et al., Specific Sorbent to Remove Solvent-Detergent Mixtures from Virus-Inactivated Biological Fluids, Journal of Chromatography, 1995, pp. 119-125, vol. 664.

Wiseman, Effect of Different Barriers of Oxidized Regenerated Cellulose (ORC) on Cecal and Sidewall Adhesions in the Presence and Absence of Bleeding, Journal of Investigative Surgery, 1999, pp. 141-146, vol. 12.

Wiseman, et al., Effect Of Thrombin Induced Hemostasis on the efficacy Of an Absorbable Adhesion Barrier, The Journal Of Reproductive Medicine, 1992, pp. 766-770, vol. 37 Issue 9.

Wiseman, et al., The Effect Of Tranexamic Acid in Fibrin Sealant on Adhesion Formation in the rat, Wiley Periodicals, Inc., Jun. 24, 2003, pp. 222-230, vol. 68B.

Written Opinion of the International Searching Authority, PCT/IL2019/000004, dated Jun. 15, 2021, 7pgs.

Buchta, et al., "Biochemical characterization of autologous fibrin sealants produced by CryoSeal® and Vivostat® in comparison to the homologous fibrin sealant product Tissucol/Tisseel", Biomaterials, 2005, pp. 6233-6241, vol. 26.

Dhillon, et al., :"Fibrin Sealant (Evicel®[Quixil®/CrossealmTM) A Review of its Use as Supportive Treatment for Haemostasis in Surgery", Drugs, 2011, pp. 1893-1915, vol. 71 issue 14.

* cited by examiner

LOW CONCENTRATED PROTEIN COMPOSITIONS FOR PREVENTING TISSUE ADHESION

BACKGROUND ART

References considered to be relevant as background to the presently disclosed subject matter are listed below:
International patent application publication No. WO9855140
U.S. Pat. No. 6,965,014
US Patent Application No. 2002/001584
U.S. Pat. No. 6,613,325
Wiseman D et al., The effect of tranexamic acid in fibrin sealant on adhesion formation in the rat. *J. Biomed. Mater. Res. B Appl. Biomater.* (2004); 68(2):222-30.

Acknowledgement of the above references herein is not to be inferred as meaning that these are in any way relevant to the patentability of the presently disclosed subject matter.

TECHNOLOGICAL FIELD

The present disclosure relates to kits comprising fibrinogen and thrombin and uses thereof for reducing and preventing tissue adhesion.

BACKGROUND

Tissue adhesion after invasive procedures often result in pain, discomfort and is even, in some cases, life threatening. Thus, reduction or prevention of such tissue adhesion is highly important.

International patent application publication No. WO9855140 discloses a fibrinogen concentrate having a fibrinogen concentration range of less than 80% of the total protein and with at least 20% of naturally occurring plasma proteins, such as fibronectin, factor VIII, von Willebrand factor, factor XIII, and vitronectin, of the total protein.

US Patent Application No. 2002/001584 discloses a fabric adhesive having stabilization in liquid or in frozen state and being stored in fibrinogen preparation, with chaotrope substance being added, where a thrombin preparation reduces or prevents the postoperative fabric adhesive diseases.

U.S. Pat. No. 6,965,014 discloses a bioerodible fibrin material which is obtained by mixing fibrinogen and thrombin reconstituted or diluted with a particular high tonic strength medium, free of calcium. Such a fibrin-based biomaterial develops a tight structure with thin fibers and small pore size suitable for use as an anti-adhesion barrier.

U.S. Pat. No. 6,613,325 discloses that a fibrin polymer film formed by applying materials most closely resembling the natural clotting materials to a surgical adhesion formation.

Wiseman D et al., describes that fibrin containing either tranexamic or aprotinin reduced the incidence and severity of adhesions.

GENERAL DESCRIPTION

The present disclosure provides, in accordance with some aspects, a kit comprising: (i) a first container comprising a solution of fibrinogen-containing component comprising fibrinogen at a concentration range of between about 5 mg/ml to about 30 mg/ml and having a total protein concentration range between about 15 mg/ml to about 40 mg/ml; and (ii) a second container comprising a solution of thrombin-containing component.

The present disclosure provides, in accordance with some aspects, a mixture comprising a fibrinogen-containing component and a thrombin-containing component, calcium ions and albumin, wherein the mixture comprises total protein is in a range of between about 10 mg/ml to about 30 mg/ml, fibrinogen in a range of between about 50% to about 80% of total protein and albumin in a range of above 0.65 mg/ml to about 3 mg/ml.

The present disclosure provides, in accordance with some others aspects, a hydrogel material comprising fibrin and calcium ions, wherein the total protein concentration ranges from between about 2.5 mg/ml to about 30 mg/ml, and the fibrin is present at a concentration range of 50 to 80% of a total protein weight.

The present disclosure provides, in accordance with some further aspects a hydrogel material comprising cross-linked fibrin, obtained by applying on a tissue (i) a fibrinogen-containing solution comprising a fibrinogen at a concentration range of between about 5 mg/ml to about 30 mg/ml and a total protein concentration range is between about 15 mg/ml to about 40 mg/ml and (ii) thrombin, under conditions allowing formation of a clot. In some embodiments, the fibrinogen-containing solution and the thrombin are mixed prior to application on the tissue. In some other embodiments, the fibrinogen-containing solution and the thrombin are applied separately on the tissue (sequentially or in parallel).

The present disclosure provides, in accordance with some further aspects a two-component composition for use in preventing tissue adhesion, comprising: component A comprising a fibrinogen-containing solution comprising a fibrinogen at a concentration range of between about 5 mg/ml to about 30 mg/ml and a total protein concentration range is between about 15 mg/ml to about 40 mg/ml; and component B comprising thrombin.

The kit, the mixture, the hydrogel and the a two-component composition are each in accordance with some aspects for use in reducing tissue adhesion.

The present disclosure provides, in accordance with some further aspects a method for reducing, preventing or inhibiting tissue adhesion, the method comprises applying a fibrinogen-containing component and a thrombin-containing component onto at least a portion of the tissue of a subject, wherein the fibrinogen-containing component comprises a total protein concentration range between about 15 mg/ml to about 40 mg/ml and fibrinogen at a concentration range of between about 5 mg/ml to about 30 mg/ml, the amounts of the fibrinogen-containing component and the thrombin-containing component are effective in reducing/preventing/inhibiting tissue adhesion when brought into contact with the tissue.

DETAILED DESCRIPTION OF EMBODIMENTS

Tissue adhesion is a natural part of a healing process after an invasive procedure. However, tissue adhesion often causes inflammation associated with pain and additional severe effects. Reducing or inhibiting adhesion after invasive procedures, is therefore, highly desired.

The present invention is based on the development of a kit that can be administered on a tissue, for example, after an invasive procedure, in order to reduce or prevent or inhibit tissue adhesion. The kit comprises at least a fibrinogen component and as detailed below can comprise an additional thrombin component. Hence, the kit described herein may comprise two components, a fibrinogen component and a thrombin component.

Kits that are fibrinogen-based are known. For example, an FDA approved kit, EVICEL®, includes a fibrinogen component that comprises 80-120 mg/ml total protein including about 55-85 mg/ml fibrinogen.

The inventors have surprisingly found that kits comprising reduced amounts of fibrinogen and more surprisingly, reduced amounts of total protein are effective in reducing/preventing adhesion after invasive procedures, as compared to known fibrinogen formulations. Specifically, and as shown in the Examples below, the formulations of the present disclosure reduced post-surgical adhesion as well as affected the water retention capability of the formed hydrogel. Based on this, the inventors suggested that while the amounts of the plasma components are reduced and subsequently the degree of the formed physical barrier (e.g. in the form of a hydrogel), the kit of the present invention exhibits superior anti-adhesive properties, e.g. in preventing/reducing/inhibiting adhesion.

The kit described herein comprises low amounts of raw material and specifically a solution of fibrinogen-containing component comprising fibrinogen and having a total protein concentration lower than 40 mg/ml. Thus, in accordance with its broadest aspect, the present disclosure provides a kit comprising a container comprising a solution of fibrinogen-containing component comprising fibrinogen at a concentration range of between about 5 mg/ml to about 30 mg/ml and having a total protein concentration range between about 15 mg/ml to about 40 mg/ml. The kit can comprise an additional thrombin component.

Thus, the present disclosure provides in accordance with some aspects, a kit comprising (i) a first container comprising a solution of fibrinogen-containing component comprising fibrinogen at a concentration range of between about 5 mg/ml to about 30 mg/ml and having a total protein concentration range between about 15 mg/ml to about 40 mg/ml; and (ii) a second container comprising a solution of thrombin-containing component. In some embodiments, the kit is an anti-adhesion kit, i.e. has adhesion prevention/reduction/inhibition properties.

As used herein and in the art, the term "fibrinogen" refers to a precursor protein of the blood clot matrix. The fibrinogen has a molecular weight of about 340,000 Daltons and consists of 3 pairs of non-identical polypeptide chains, Aα, Bβ and γ, linked together by disulfide bonds. Typically, fibrinogen has a trinodular structure: two identical D terminal globular domains and a central E globular domain connected by supercoiled α-helices.

The "fibrinogen-containing component" is to be understood as a formulation comprising a priori fibrinogen. The fibrinogen-containing component is an aqueous formulation. The "aqueous formulation" encompass a blend of ingredients, in liquid form or frozen form, that contains water molecules. In some embodiments, the aqueous formulation is in liquid form. When in liquid form, it is in accordance with some embodiments that the liquid carrier is a buffer having an essentially neutral pH, e.g. pH 7.0±0.5. In some embodiments, the fibrinogen-containing component is frozen. Prior to use, the fibrinogen-containing component can be thawed and thereby turn into liquid form at room temperature. The formulation can be in the form of solution.

The term "liquid" relates to a substance that can flow, has not fixed shape, and is not a solid or gas. The term "solution" relates to dispersed or dissolved substance(s) and the medium in which it is dispersed or dissolved or to a single homogeneous liquid phase that is a mixture in which the components are uniformly distributed throughout the mixture.

The term "component" relates to any ingredient which may be present in a product, such as a drug product.

In some embodiments, the fibrinogen-containing component comprises total protein at a concentration range between about 15 mg/ml to about 40 mg/ml. In some embodiments, the fibrinogen-containing component comprises total protein at a concentration range between about 30 mg/ml to about 40 mg/ml. In some embodiments, the fibrinogen-containing component comprises total protein at a concentration range between about 20 mg/ml to about 25 mg/ml. In some embodiments, the fibrinogen-containing component comprises total protein at a concentration range between about 35 mg/ml to about 40 mg/ml. In some embodiments, the fibrinogen-containing component comprises total protein at a concentration range between about 15 to 36 mg/ml. In some embodiments, the fibrinogen-containing component comprises total protein at a concentration range between about 20 to 36 mg/ml. In some embodiments, the fibrinogen-containing component comprises total protein at a concentration range between about 20 to 40 mg/ml.

Total protein may be determined by any method known in the art. For example, by measuring absorbance at 280 nm (UV range).

In some embodiments, the fibrinogen-containing component comprises fibrinogen at a concentration of 5, 6, 7, 8, 9, 10, 11, 12, 13, 14, 15, 16, 17, 18, 19, 20, 21, 22, 23, 24, 25, 26, 27, 28, 29, or 30 mg/ml, including any value and range therebetween. In some embodiments, the fibrinogen-containing component comprises fibrinogen at a concentration range of between about 8 mg/ml to about 25 mg/ml. In some embodiments, the fibrinogen-containing component comprising fibrinogen at a concentration range of between about 11 mg/ml to about 25 mg/ml. In some embodiments, the fibrinogen-containing component comprising fibrinogen at a concentration range of about 11 mg/ml to about 15 mg/ml. In some embodiments, the fibrinogen-containing component comprising fibrinogen at a concentration range of about 20 mg/ml to about 25 mg/ml. In some embodiments, the fibrinogen-containing component comprising fibrinogen at a concentration range of about 11 mg/ml to about 23 mg/ml. In some embodiments, the fibrinogen-containing component comprising fibrinogen at a concentration range of about 9 mg/ml to about 14 mg/ml In some embodiments, the fibrinogen-containing component comprises one or more additional factors selected from, without being limited thereto, factor XIII, factor VIII, fibronectin, von Willebrand factor (vWF), and vitronectin.

In some embodiments, the fibrinogen-containing component comprises fibrinogen at a weight concentration in a range of between about 50% to about 80% of total protein.

The fibrinogen in the fibrinogen-containing component can be purified and isolated from plasma. Fibrinogen containing component can be a biologically active component (BAC) such as a fibrinogen concentrated viral-inactivated cryoprecipitate from human plasma comprising solution. BAC comprises blood plasma derived proteins. The term "derived" relates to received from a source. For example, "derived from" relates to taken from, obtained from, received from.

In some embodiments, the fibrinogen comprises plasma cryoprecipitated fibrinogen. In some embodiments, the fibrinogen is originated (or derived) from plasma cryoprecipitated fibrinogen. In the context of the present disclosure, the term "cryoprecipitated fibrinogen" refers to fibrinogen obtained from frozen plasma, typically the latter prepared from whole blood (also denoted as fibrinogen is obtained by plasma cryoprecipitation).

In some embodiments, cryoprecipitated fibrinogen is obtained when frozen plasma thawed in the cold, typically at a temperature of 0-4° C., resulting in the formation of a precipitate that comprises predominantly the fibrinogen. In some embodiments, the cryoprecipitate is collected, for example by centrifugation and is then dissolved in a suitable buffer such as a buffer containing 120 mM sodium chloride, 10 mM trisodium citrate, 120 mM glycine, or 95 mM arginine hydrochloride.

In some embodiments, the cryoprecipitated fibrinogen is regarded as the biologically active component (BAC) of blood plasma. In some embodiments, the BAC is viral inactivated. There are several types of BAC. In some embodiments, BAC is a biologically active component that contains tranexamic acid, as an antifibrinolytic agent.

In some embodiments, the fibrinogen is provided as part of the biologically active component (BAC). Non-limiting preparation routes of BAC are described in U.S. Pat. No. 6,121,232 and/or WO98/033533 the contents of which is incorporated by reference.

In some embodiments, a BAC composition comprises one or more anti-fibrinolytic agents (e.g., tranexamic acid) and arginine hydrochloride.

In some embodiments, the concentration range of the anti-fibrinolytic agent such as tranexamic acid in the BAC ranges from about 80 to about 110 mg/ml.

In some embodiments, the fibrinogen-containing component does not contain tranexamic acid. In some embodiments, the fibrinogen-containing component does not contain aprotinin. In some embodiments, the fibrinogen-containing component is biologically active component that does not contain tranexamic acid or aprotinin. During BAC2 preparation, plasminogen (the enzyme precursor of plasmin, which breaks down fibrinogen and fibrin) and/or plasmin is removed and therefore BAC2 does not contain tranexamic acid or aprotinin.

In some embodiments, BAC is Biologically active component 2 (BAC2), i.e. a biologically active component that lacks tranexamic acid. BAC2 is a concentrated viral-inactivated cryoprecipitate of human plasma (the cryoprecipitate is typically prepared as described in EP 534,178) which consists mainly of fibrinogen (approx. 85%) and is plasminogen-depleted (the removal of plasminogen is typically carried out as described in EP 1,390,485) and without anti-fibrinolytic agents added. In view of removal of plasmin/plasminogen from the cryoprecipitate, there is no need to add anti-fibrinolytic agents, such as tranexamic acid, aprotinin or the like.

Accordingly, in some embodiments, the fibrinogen component is derived from BAC2 which is depleted from plasmin(ogen) and does not comprise tranexamic acid or aprotinin.

In some embodiments, the fibrinogen is a biologically active component of a plasma cryoprecipitate-derived from antihaemophilic factor preparation. An Antihemophilic factor is a naturally occurring protein in the blood that helps blood to clot.

In some embodiments, fibrinogen is purified from an aluminum hydroxide precipitate from a byproduct in the manufacture process of factor VIII (FVIII) as disclosed in WO2013/001524A1.

The BAC solution can further comprise stabilizers such as arginine, lysine and other sealant additives as known in the art. In some embodiments, BAC and preferably BAC2 is derived from plasma cryoprecipitate (in particular concentrated cryoprecipitate).

Examples of fibrinogen sources include, but are not limited to, recombinant fibrinogen, plasma purified fibrinogen, including fibrinogen component of EVICEL® (i.e, BAC2), fibrinogen component of Tisseel (containing aprotinin, an antifibrinolytic agent).

In some embodiments, the blood derived fibrinogen concentrate is a byproduct of the manufacture process of factor VIII and may be selected from acid-precipitate, chill-precipitate, aluminum hydroxide precipitate (see, for example, U.S. Pat. No. 4,455,300, the content of which is incorporated herein by reference), glycine precipitate (see, for example, U.S. Pat. No. 4,297,344, the content of which is incorporated herein by reference), ethanol precipitate, and heparin precipitated paste.

In some embodiments, plasma cryoprecipitated fibrinogen denotes, without being limited thereto, fresh frozen plasma precipitate following centrifugation containing total protein in the range of 30 to 60 mg/ml; total viable count (TVC) <1000 CFU/ml; Factor XIII, 2 to 9 IU/ml; Fibronectin—0.5 to 6 mg/ml; and Colttable Fibrinogen—18 to 39 mg/ml.

In yet some other embodiments, the blood derived fibrinogen concentrate comprises or is suspended or precipitated Cohn Fraction I, at times, also referred to as "Paste I".

In some embodiments, Cohn fractionation is a process exploiting differences in isoelectric properties of the various plasma proteins and comprises a series of purification steps that involve modifying the pH, ethanol concentration and temperature to separate proteins through precipitation into five "fractions" (I-V). The Cohn process is known also as the cold ethanol precipitation and is described, e.g. in U.S. Pat. No. 2,390,074, and by Cohn et al. (J. Am. Chem. Soc. 68:459, 1945, J. Am. Chem. Soc. 72:465-474, 1950). Notably, in the context of the present disclosure, when referring to "suspended or precipitated Cohn Fraction I" it is to be understood as encompassing any product of ethanol fractionation whereby at least fibrinogen is precipitated, and not only the Cohn process referred to hereinabove.

In some embodiments, to obtain suspended or precipitated Cohn Fraction I, blood plasma is subjected to ethanol concentration. Specifically, Cohn I precipitate (Fraction I) may be obtained from thawed pooled plasma by precipitation e.g., at −3° C. to −5° C. and neutral pH at 8-10% ethanol concentration.

Fibrinogen concentrate may also be obtained commercially. Examples of fibrinogen include, but are not limited to, fibrinogen component of EVICEL® (i.e. BAC2), fibrinogen component of Tisseel (containing aprotinin, an antifibrinolytic agent).

In some embodiments, the fibrinogen-containing component is diluted BAC2. As noted above BAC2 does not include tranexamic acid or aprotinin. It was previously considered that tranexamic acid and/or aprotinin are required for reducing tissue anti-adhesion. It was surprisingly found that although the fibrinogen-containing component (i.e. diluted BAC2) does not contain tranexamic acid or aprotinin, an efficient anti-adhesion activity was observed.

In some embodiments, the fibrinogen-containing component comprises BAC2 diluted by at least a factor of two. In some embodiments, the fibrinogen-containing component comprises BAC2 diluted by a factor of between two to ten. In some embodiments, the fibrinogen-containing component comprises BAC2 diluted by a factor of two. In some embodiments, the fibrinogen-containing component comprises BAC2 diluted by a factor of four. In some embodiments, the fibrinogen-containing component comprises BAC2 diluted by a factor of eight.

A variety of buffers may be used for the dilution of fibrinogen-containing component. In some embodiments, the buffer comprises at least one of sodium chloride, tri-sodium citrate dihydrate, glycine, arginine hydrochloride and calcium chloride dihydrate. In some embodiments, the buffer comprises about 120 mM sodium chloride, about 10 mM tri-sodium citrate dihydrate, about 120 mM glycine, about 9.5 mM arginine hydrochloride and about 1 mM calcium chloride dihydrate. In some embodiments, the buffer has a pH value of 7.0-7.2. An exemplary buffer is as shown in Table 2 below.

In some embodiments, the dilution buffer of the fibrinogen-containing component (solution) does not comprise albumin.

As appreciated, In BAC2 in the absence of albumin in the dilution buffer, the amount of albumin in the fibrinogen-containing component is determined by the dilution factor of BAC2.

In some embodiments, the fibrinogen-containing component essentially does not include albumin. In such embodiments, the thrombin containing component may comprise albumin.

In some embodiments, the thrombin-containing component essentially does not include albumin. In such embodiments, the fibrinogen containing component may comprise albumin.

In such some embodiments, the fibrinogen-containing component has an albumin concentration range lower than 20% by weight of total protein. In some embodiments, the fibrinogen-containing component has an albumin concentration range lower than 15% by weight of total protein. In some embodiments, the fibrinogen-containing component has an albumin concentration range lower than 10% by weight of total protein. In some embodiments, the fibrinogen-containing component has an albumin concentration range lower than 11% by weight of total protein. In some embodiments, the fibrinogen-containing component has an albumin concentration range lower than 5% by weight of total protein. In some embodiments, the fibrinogen-containing component has an albumin concentration range between about 2% to about 17% by weight of total protein, at times between about 10% and 15% by weight of total protein, at times between about 5% to to about 15% by weight of total protein, at times between about 8% to about 10% by weight of total protein, at times between about 8% to about 12% by weight of total protein.

In some embodiments the fibrinogen containing component essentially does not include albumin. By referring to "essentially does not include albumin" it is meant to comprising albumin at an amount that is less 0.65 mg/ml.

The fibrinogen-containing component may comprise plasma proteins other than fibrinogen and albumin. In some embodiments, the plasma proteins other than fibrinogen may be present. Non-limiting examples of plasma proteins other than fibrinogen and albumin include naturally occurring plasma proteins, such as fibronectin, factor VIII, von Willebrand factor, factor XIII, and vitronectin.

As noted herein, the kit comprises a second compartment comprising thrombin. Thrombin is a mammalian serine protease which is part of the blood coagulation cascade and converts fibrinogen into insoluble strands of fibrin, as well as catalyzes other coagulation-related reactions. In the context of the present disclosure, the term "thrombin" is also meant to encompass thrombin functional analog. The term "thrombin functional analog" refers to an entity that is capable of at least cleaving fibrinogen to form fibrin.

The "thrombin-containing component" is to be understood as a formulation comprising a priori thrombin an optionally additional proteins such as albumin. The thrombin-containing component may be in a liquid form or in a frozen form. The thrombin-containing component may be manipulated before use, for example by thawing if present in a frozen form.

In some embodiments, the thrombin-containing component comprises between about 100 IU/ml to about 300 IU/ml thrombin. In some embodiments, the thrombin-containing component comprises between about 100 IU/ml to about 200 IU/ml thrombin. In some embodiments, the thrombin-containing component comprises between about 150 IU/ml to about 200 IU/ml thrombin. As used herein, the term "IU" denotes "International Units" and may be determined by the clotting assay against an internal reference standard for potency concentration measurement that has been calibrated against, for example, the World Health Organization (WHO) Second International Standard for Thrombin, 01/580. A unit (U) is equivalent to an International Unit (IU).

In some embodiments, the thrombin-containing component comprises a diluted thrombin component of EVICEL®. In some embodiments, the thrombin-containing component comprises the thrombin component of EVICEL® diluted by at least a factor of two. In some embodiments, the thrombin-containing component comprises the thrombin component of EVICEL® diluted by a factor of between two to ten. In some embodiments, the thrombin-containing component comprises the thrombin component of EVICEL® diluted by a factor of two. In some embodiments, the thrombin-containing component comprises the thrombin component of EVICEL® diluted by a factor of four. In some embodiments, the thrombin-containing component comprises the thrombin component of EVICEL® diluted by a factor of eight.

A variety of buffers may be used for the dilution of thrombin-containing component. In some embodiments, the buffer comprises at least one of sodium acetate trihydrate, D-mannitol, calcium chloride dihydrate and sodium chloride. In some embodiments, the buffer comprises about 20 mM sodium acetate trihydrate, about 0.1 mM D-mannitol, about 40 mM calcium chloride dihydrate and about 90 mM sodium chloride. In some embodiments, the buffer has a pH value of 6.8-7.2. An exemplary buffer is as shown in Table 3 below.

In some embodiments, the dilution buffer of the thrombin-containing component does not comprise albumin.

In some embodiments the thrombin containing component essentially does not include albumin. By referring to "essentially does not include albumin" it is meant to comprising albumin at an amount that is less 0.65 mg/ml.

As appreciated, in the absence of albumin in the dilution buffer, the amount of albumin in the thrombin-containing component is determined by the dilution factor of thrombin.

In some embodiments, the thrombin-containing component includes albumin. In such embodiments, the thrombin-containing component may comprise albumin. In some embodiments, the thrombin-containing component comprises up to about 6 mg/ml albumin. In some embodiments, the thrombin-containing component comprises 1 up to about 6 mg/ml albumin. Thrombin converts fibrinogen into fibrin that undergoes spontaneous polymerization. As such, the two components, the fibrinogen-containing component and the thrombin-containing component are brought into contact to allow the anti-adhesion activity.

The two components may be mixed prior to application of a tissue or alternatively each one of the two components may be applied on the same tissue separately such that the mixing of the two takes place on the tissue.

In some embodiments, the fibrinogen-containing component and the thrombin-containing are mixed at a ratio of between 0.8:1.2 to about 1:2:0.8, respectively, at times about 1:1. In some embodiments, the fibrinogen-containing component and the thrombin-containing are mixed prior to application on a tissue. Mixing the two components prior to application is denoted herein as an anti-adhesive mixture. It is appreciated that mixing these two components results in formation of a hydrogel (as discussed below) and is applied on a tissue within a time frame to allow it's use, typically up to 1 or 1.5 minutes. As also appreciated, the mixture is applied on the tissue to allow clot formation.

In some embodiments, the fibrinogen-containing component and the thrombin-containing component are applied separately on a tissue and are mixed thereon to form a gel. As also appreciated, application of the two components onto the tissue allow clot formation.

The mixture (i.e. mixed prior to application) or the formed hydrogel (i.e. from the mixture or when applied directly on a tissue) of the fibrinogen-containing component and the thrombin-containing (herein also referred to as: "combined components") comprise an albumin concentration higher than 0.65 mg/ml to about 3 mg/mL; at times equal or above 1.2 mg/ml; at times equal or above 1.25 mg/ml; at times equal or lower than 3 mg/ml; at times equal or above 1.5 mg/ml, at times equal or lower than 3 mg/ml.

In some embodiments, the albumin in the combined components is lower than 20% by weight of total protein in the combined components. In some embodiments, the combined fibrinogen-containing component and thrombin-containing component comprises between about 6.5% to below 20% albumin by weight of total protein, e.g. between equal to 6.5% up to equal to 17% albumin by weight of total protein.

In some embodiments, the total albumin of the combined fibrinogen-containing component and the thrombin-containing component is about 1.5 to 3 mg/ml.

In some embodiments, the total albumin of the combined fibrinogen-containing component and the thrombin-containing component is about 1.5, 2, 2.5, or 3 mg/ml, including any value and range therebetween.

In some embodiments, the total albumin of the combined fibrinogen-containing component and the thrombin-containing component is in the range of above 0.65 to 3 mg/ml.

In some embodiments, the total albumin of the combined fibrinogen-containing component and the thrombin-containing component is about 0.7, 1, 1.2, 1.25, 1.5, 2, 2.5, or 3 mg/ml, including any value and range therebetween.

In some embodiments the combined fibrinogen containing component and thrombin containing component essentially does not include albumin. By referring to "essentially does not include albumin" it is meant to comprising albumin at an amount that is less 0.65 mg/ml.

For the combined components, either mixed prior to application or applied directly on the tissue, to form of a stable clot, cross linking of polymerized fibrin is required. Such cross linking of polymerized fibrin takes place by the action of Factor XIII, activated by thrombin, in the presence of divalent ions such as calcium ions. In other words, for formation of a stable clot, the presence of calcium ions is required. The fibrinogen-containing component and/or the thrombin-containing component comprises free calcium ions. In some embodiments, the free calcium ions are ionized and non-chelated calcium.

In some embodiments, the fibrinogen-containing component comprises solubilized calcium at a concentration range between about 0.5 to about 204. In some embodiments, the fibrinogen-containing component comprises solubilized calcium at a concentration range between about 0.5 to about 1 µM. In some embodiments, the fibrinogen-containing component comprises solubilized calcium at a concentration range between about 1 to about 2 µM.

In some embodiments, the thrombin-containing component comprises solubilized calcium at a concentration range between about 30 to about 50 µM. In some embodiments, the thrombin-containing component comprises solubilized calcium at a concentration range between about 30 to about 40 µM. In some embodiments, the thrombin-containing component comprises solubilized calcium at a concentration range between about 40 to about 50 µM.

Calcium may be present in, or be originated from, one or more calcium salts including, without being limited thereto, calcium chloride, calcium acetate, calcium lactate, calcium oxalate, calcium carbonate, calcium gluconate, calcium phosphate, calcium glycerophosphate, or any combination thereof. In some embodiments, the calcium salt is calcium chloride. In some embodiments, the calcium cation is originated from calcium chloride, i.e. the formulation is prepared with calcium chloride.

In some embodiments, the calcium is non-chelated calcium. As used herein, the terms "chelated" or "chelation" in the context of non-chelated calcium refer to the formation or presence of one or more bonds, or other attractive interactions, between two or more binding sites within a chelating agent and a calcium species. The term "chelating agent" as used herein is also meant to encompass calcium precipitation agent. In some embodiments, the precipitation agent generates insoluble salt of calcium ions. In exemplary embodiments, by "non-chelated calcium" it is meant to refer to calcium ions which are present in a medium devoid of precipitation agents, such as Phosphate buffered saline (PBS). Typically, PBS comprises a water-based salt solution containing disodium hydrogen phosphate, sodium chloride and, in some formulations, potassium chloride and potassium dihydrogen phosphate. In exemplary embodiments, the components of fibrinogen and/or thrombin are devoid of chelating agents such as PBS.

The kit according with the present invention comprises two components, being separated one from the other. In other words, each one of the two components is confined in a separated container. In some embodiments, the fibrinogen-containing component and/or the thrombin-containing component may be in the form of an applicator. In some embodiments, the applicator comprises a barrel holding the fibrinogen-containing component and/or the thrombin-containing component disclosed herein and a re-sealable opening for delivery therethrough of the fibrinogen-containing component and/or the thrombin-containing component.

In some embodiments, the applicator is a syringe. Application may be by pushing each one of the components out of the syringes and either mixed, for example, into a common conduit, to form a composition (mixture), out of which the mixture is thereafter directly applied to the tissue or alternatively to be directly applied to a desired target site or directly applied on the tissue.

The fibrinogen-containing component and/or the thrombin-containing component may be in liquid form, in a lyophilized form or in dry form, the latter is to be wetted (e.g. with saline) prior to application.

In some embodiments, the fibrinogen-containing component and/or the thrombin-containing component may be applied at a tissue to be treated used by, for example, spraying or dripping.

The applicator can be for single use, i.e. to be disposed after all or a portion of the fibrinogen-containing component and/or the thrombin-containing component is used; or it may be designed for multiple uses such that the applicator's opening is resealed between uses.

Once the combined components (fibrinogen and thrombin) are brought into contact (mixture or direct application), clotting initiates and fibrin clot-based tissue adhesive is formed. Thus, application of fibrinogen-containing component and the thrombin-containing component (mixture or direct application) results in formation of a sealant formulation. In the context of the present invention, the term "sealant formulation" is to be understood as a formulation having ingredients that upon contact react to subsequently form a tissue adhesive.

Thus, the present disclosure relates in some aspects to a two-component composition for use in preventing tissue adhesion, comprising a first component (component A) comprising a fibrinogen-containing solution comprising a fibrinogen at a concentration range of between about 5 mg/ml to about 30 mg/ml and a total protein concentration range is between about 15 mg/ml to about 40 mg/ml and a second component (component B) comprising a thrombin.

Application of the fibrinogen-containing component and the thrombin-containing composition on a target tissue (either by mixing a-priori or not as described herein above) results in formation of a gel having an increased viscosity as compared to each one of the individual components. Such increased viscosity is a result of "curing" and may be obtained by interactions including polymerization and/or cross-linking of protein components (e.g., fibrin) in the composition. The temperature at which the curing reaction may be conducted may be at around the room temperature (e.g., 15 to 30° C.). In some embodiments, the may be in the range of seconds and up to 600 seconds. The term "curing time" means the time until an endpoint of the curing is reached.

The term "gel" refers to substantial liquid dispersed in a solid. Typically, a gel has properties of the solid state, and under certain conditions (e.g., temperature, pH) exhibits properties of the liquid state. In some embodiments, the gel is a hydrogel. The term "hydrogel" is intended to refer to hydrophilic polymeric networks having water content In some embodiments, the curing is carried out spontaneously at ambient conditions.

In some embodiments, the curing is implemented by one or more methods including, without being limited thereto: by use of an activator (such as a catalyst), by a physical activating agent, such as heat, or ultra-violet (UV) radiation. Thus, the present disclosure provides in accordance with some aspects a hydrogel material comprising fibrin, calcium, wherein the total protein concentration ranges from between about 2.5 mg/ml to about 30 mg/ml, the fibrin is present at a concentration range of 50 to 80% of a total protein weight.

In some embodiments, the fibrin in the hydrogel is a cross-linked fibrin.

In some embodiments, the total protein concentration in the hydrogel ranges from between about 7.5 mg/ml to about 20 mg/ml.

In some embodiments, the total protein concentration in the hydrogel ranges from between about 5.5 mg/ml to about 10 mg/ml.

As described herein, the formed hydrogel has anti-adhesive properties.

In some embodiments, the albumin is present at the hydrogel at a concentration of about 1.5 to 3 mg/ml. In some embodiments, the albumin is present at the hydrogel at a concentration is equal to or above 1.25 mg/ml and up to and equal to 3 mg/ml. In some embodiments, the albumin is present at the hydrogel at a concentration is equal to or above 1.20 mg/ml and up to and equal to 3 mg/ml. In some embodiments, the albumin is present at the hydrogel at a concentration is above 0.65 mg/ml and up to and equal to 3 mg/ml.

As shown in the Examples below, water retention in the hydrogel is affected by the kit of the invention. The hydrogel formed by kits of the present invention retains a higher proportion of water than fibrin materials currently available. The greater degree of water retention is particularly beneficial to the therapeutic use of the hydrogel. Without being bound by any particular mechanism, the greater degree of water retention is indicative of the strong structure of the gel or barrier. Such a gel is capable to retain water despite being subjected to high pressure, compression, or impact stress e.g. by a neighboring tissue. The retention of water is beneficial for the control of the concentration of therapeutic agents that may be contained within the fibrin hydrogel, as well as for the effective release of these therapeutic agents and additives. The ability of fibrin hydrogels to retain water while being subjected to compression forces was tested and compared to the water retaining capacity of a classic fibrin material. In particular, compression was applied by centrifugation of the materials at various rotational speeds and the amount of water retained was measured. A refrigerated centrifuge (Sorvall RT 6000B) spun fibrin hydrogels at different speeds.

In some embodiments, the hydrogel is characterized in that it retains at least 70%, the initial water content upon applying on a surface thereof a pressure of about 400-500 PSI.

In some embodiments, the hydrogel is characterized in that it retains at least 70%-80%, the initial water content upon applying on a surface thereof a pressure of about 400-500 PSI.

In some embodiments, the hydrogel is characterized in that it retains at least 70%, the initial water content upon applying on a surface thereof a pressure of about 400-500 PSI.

In some embodiments, the hydrogel is characterized in that it retains at least about 80% to 95%, the initial water content upon applying on a surface thereof a pressure of about 400-500 PSI.

In accordance with some aspects, the present disclosure provides a hydrogel material comprising cross linked fibrin, obtained by applying on a tissue a mixture comprising (i) a fibrinogen-containing solution comprising a fibrinogen at a concentration range of between about 5 mg/ml to about 30 mg/ml and a total protein concentration range is between about 15 mg/ml to about 40 mg/ml and (ii) thrombin, under conditions allowing forming cross linked polymerized fibrin in/on the tissue. In some embodiments, the mixture comprises free calcium ions. In some embodiments, the mixture is obtained by combining ex vivo the fibrinogen-containing solution and the thrombin.

As described above, the kit of the present disclosure has a significant improved anti-adhesion effect when applied on a target tissue.

Thus, in yet another aspect, the invention provides a method for reducing or preventing or inhibiting adhesion in a tissue, the method comprising applying onto at least a portion of the tissue of a subject, a fibrinogen-containing component and a thrombin-containing component, wherein the fibrinogen-containing component comprises a total protein concentration range between about 15 mg/ml to about 40 mg/ml and fibrinogen at a concentration range of between about 5 mg/ml to about 30 mg/ml, the amounts of the fibrinogen-containing component and the thrombin-containing component are effective in reducing or preventing tissue adhesion when brought into contact with the tissue. The term "effective amount" as used herein is that determined by such considerations as are known to the man of skill in the art.

In some embodiments, the tissue is a wounded/injured tissue. The injured tissue may be due to surgery, trauma, infection, or radiation. The injury of a tissue may be related to any physiological process that may for example, trigger macrophages and/or fibroblasts for a healing process.

The adhesion to be reduced/prevented by the kit may be following an invasive procedure. As used herein, the term "anti-adhesive" refers to preventing or reducing adhesion in a tissue or at a proximity of the tissue. The Anti-adhesive composition refers to a composition which can prevent or reduce adhesion, such adhesions (e.g. post-operative adhesions) which may result from complications appearing after invasive procedures in a tissue or at a proximity of the tissue.

In some embodiments of the method, the anti-adhesive effect may be exerted by applying the anti-adhesive to a target area and optionally covering adhesion areas or possible adhesion areas with the anti-adhesive to inhibit the adhesion. In some embodiments, the anti-adhesive may be applied to a target area, and the other desired area is attached thereto, which is then allowed to stand or pressed for a certain period of time.

Typically, for anti-adhesion applications at the target site, e.g., surgical site, the disclosed composition allows to provide a durable physical barrier between different organs at the surgical site. The term "durable", in the context of anti-adhesion applications, is meant to refer to providing sturdy physical barrier as described above for a duration of at least 1 day, at least 2 days, at least 3 days, at least 4 days, at least 5 days, at least 6 days, at least 7 day, at least 8 days, at least 9 days, at least 10 day, at least 11 days, at least 12 days, at least 13 days, or at least 14 days, e.g., 1 to 14 days.

The term "adhesion" is generally applied to describe the formation of a scar that extends from within one tissue across to another, usually across a virtual space such as the peritoneal cavity. Adhesion formation after an invasive procedure usually occur when two injured surfaces are close to one another and this may cause inflammation and causes fibrin deposits onto the damaged tissues. Adhesion formation may create an interface between tissue that are often not joined together. The adhesions themselves are painless, however, adhesion related complications may occur, causing, for example, pain and obstruction. As noted above, the inventors have surprisingly found that the kit of the present invention which comprises reduced amounts of fibrinogen is effective in reducing/inhibiting tissue adhesion.

The present disclosure is not limited to a specific injured/wounded tissue. Non-limiting examples of tissues may be, for example from abdominal, cardiac tissue, thoracic tissue, from head, from neck, pelvic tissue, skin tissue. In some embodiments, the method is for reducing/preventing tissue adhesion after an abdominal surgery, cardiovascular surgery or a pelvic surgery.

In some embodiments, the injured tissue is not a bleeding tissue.

In some other embodiments, the method is for preventing or reducing tissue adhesion during an invasive procedure.

The invasive procedure may be according with some embodiments a surgical procedure.

There are many surgical procedures in which the methods and kits of the present disclosure can be used, such as, without being limited thereto, abdominal surgery, cardiovascular surgery, thoracic surgery, head and neck surgery, pelvic surgery, skin and subcutaneous tissue procedure. In some embodiments, the method is for reducing/preventing tissue adhesion after an abdominal surgery, cardiovascular surgery or a pelvic surgery.

The term abdominal surgery encompasses a surgical procedure involving opening of the abdominal (laparotomy). Non-limiting examples of abdominal surgery may include appendectomy, Caesarean section, Exploratory laparotomy or Laparoscopy.

The invasive procedure may be in accordance with some other embodiments, a diagnostic procedure.

In some embodiments, the method is for a human subject.

The fibrinogen-containing component and a thrombin-containing component may be mixed prior to the application on the target tissue or administered simultaneously on the target tissue. In some embodiments, application on the target tissue comprise spraying or dripping spraying, smearing, brushing, or injecting. It should be appreciated that the terms "inhibition", "moderation", "reduction", "decrease" or "attenuation" or "prevention" or "diminishing" a process (such as tissue adhesion, for example) as referred to herein, relate to a phenomenon or a phenotype by at least about 1%-100%, about 5%-95%, about 10%-90%, about 15%-85%, about 20%-80%, about 25%-75%, about 30%-70%, about 35%-65%, about 40%-60% or about 45%-55%. The inhibition, moderation, attenuation, restriction, prevention, retardation, reduction, decrease or diminishing of a process, a phenomenon or a phenotype (such as tissue adhesion) may also be by at least about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or about 100%.

The term "about" as used herein indicates values that may deviate up to 1%, more specifically 5%, more specifically 10%, more specifically 15%, and in some cases up to 20% higher or lower than the value referred to, the deviation range including integer values, and, if applicable, non-integer values as well, constituting a continuous range.

The terms "comprises", "comprising", "includes", "including", "having", and their conjugates mean "including but not limited to". The term "consisting of" means "including and limited to". The term "consisting essentially of" means that the composition, method or structure may include additional ingredients, steps and/or parts, but only if the additional ingredients, steps and/or parts do not materially alter the basic and novel characteristics of the claimed composition, method or structure.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

In those instances where a convention analogous to "at least one of A, B, and C, etc." is used, in general such a construction is intended in the sense one having skill in the art would understand the convention (e.g., "a composition having at least one of A, B, and C" would include but not be limited to compositions that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

The invention will now be exemplified in the following description of experiments that were carried out in accordance with the invention. It is to be understood that these examples are intended to be in the nature of illustration rather than of limitation. Obviously, many modifications and variations of these examples are possible in light of the above teaching.

NON-LIMITING EXAMPLES

Example 1

Water Retention Under Different Conditions

This study was aimed to quantitate the % water retention in clots that were formed using various formulations and to evaluate the effect of albumin on the % water retention. Each one of the experiments included combining of two different components denoted herein as fibrinogen component and thrombin component (0.5 ml of each component).

The two components, BAC2 and thrombin (without the dilutions) are collectively known as the components in the product EVICEL®. Table 1 summarizes the formulations that were tested. The fibrinogen component and the thrombin component refer to each one of these components separately, whereas hydrogel refers to the albumin concentration (mg/ml) in the combined two components (either prior to, or after application on a tissue).

TABLE 1

Details of the various experimental formulations

| Hydrogel (albumin mg/ml) 9 | Exp. No. | Fibrinogen component Fibrinogen material BAC2 + albumin 12 mg/ml | Dilution buffer | Thrombin component Thrombin material + albumin 6 mg/mL | Dilution buffer |
|---|---|---|---|---|---|
| 48.2 | 1 | BAC2 (1:4 diluted) + albumin 90.4 mg/ml | With albumin 11% (110 mg/ml) | Thrombin (1:4 diluted) + Albumin | With 6 mg/mL albumin 0.6% With calcium |
| 52.5 | 2 | BAC2 (1:8 diluted) + albumin 99 mg/ml | | | |

TABLE 1-continued

Details of the various experimental formulations

| Hydrogel (albumin mg/ml) 9 | Exp. No. | Fibrinogen component Fibrinogen material BAC2 + albumin 12 mg/ml | Dilution buffer | Thrombin component | | |
|---|---|---|---|---|---|---|
| | | | | Thrombin material + albumin 6 mg/mL | Dilution buffer | |
| 1.8 | 3 | BAC2 (1:4 diluted) + albumin 2.4 | Without (W/O) albumin | 6 mg/mL | With albumin 1.2 mg/ml | With calcium |
| 1.25 | 4 | BAC2 (1:8 diluted) + albumin 1.3 | | | | |
| 48.2 | 5 | BAC2 (1:4 diluted) + albumin 90.4 mg/ml | With albumin 11% (110 mg/ml) | | With albumin 6 mg/ml 0.6% | W/O calcium, 5 mM EDTA |
| 52.5 | 6 | BAC2 (1:8 diluted) + albumin 99 mg/ml | | | | |
| 1.8 | 7 | BAC2 (1:4 diluted) + albumin 2.4 | Without (W/O) albumin | | With albumin 1.2 mg/ml | W/O calcium, 5 mM EDTA |
| 1.25 | 8 | BAC2 (1:8 diluted) + albumin 1.3 | | | | |
| 45.2 | 9 | BAC2 (1:4 diluted) + albumin 90.4 mg/ml | With albumin 11% (110 mg/ml) | TH04 100-300 IU/ml | W/O albumin No albumin (0) | W/O calcium, 5 mM EDTA |
| 49.5 | 10 | BAC2 (1:8 diluted) + albumin 99 mg/ml | | | | |
| 1.2 | 11 | BAC2 (1:4 diluted) + albumin 2.4 | W/O albumin | | | |
| 0.67 | 12 | BAC2 (1:8 diluted) + albumin 1.3 | | | | |

In this experiment, the fibrinogen material that was used is an FDA approved commercially material, denoted as BAC2 that was diluted as indicated in Table 1. BAC2 (biologically active component 2), is a fibrinogen containing product supplied by Omrix Biopharmaceuticals Ltd. BAC2 comprises about 70 mg/ml fibrinogen and a total protein concentration of 80-120 mg/ml (about 100 mg/ml). For the purpose of this study, BAC-2 samples were thawed and diluted by 1:4=fibrinogen of about 14 mg/ml or by 1:8=fibrinogen of about 8 mg/ml with either albumin-based buffer solution or albumin-free buffer solution. These fibrinogen solutions were diluted 1:1 with the thrombin component to obtain mix final solutions of about 7 mg/ml (for 1:4) and 4 mg/ml (for 1:8)). For the dilutions with buffer without albumin: total protein concentration before mixing with Thrombin was about 20 mg/ml (1:4) and 11 mg/ml (1:8). Total Protein in after mixing 1:1 with thrombin was about 10 and 5.5 Table 2 detail the components of the albumin-based buffer solution and the albumin-free buffer solution that were used for dilution of BAC-2, respectively.

The concentration of albumin in BAC-2 is about 12 mg/ml and in thrombin is about 6 mg/ml (in TH04 there is no albumin) and thus in the formulations that are diluted with an albumin free solution, the albumin concentration is as indicated in Table 5.

TABLE 2

BAC-2 albumin-based and albumin-free buffer solutions*

| Reagent | albumin-based BAC2 buffer Concentration | albumin-free BAC2 buffer |
|---|---|---|
| Sodium Chloride | 120 mM | 120 mM |
| Tri-Sodium Citrate dihydrate | 10 mM | 10 mM |
| Glycine | 120 mM | 120 mM |
| Arginine hydrochloride | 9.5 mM | 9.5 mM |
| Calcium chloride dihydrate | 1 mM | 1 mM |
| Human albumin | 11% | |
| pH | 7.0-7.2 | 7.0-7.2 |

*Instead of Albumin water for injection (WFI) was added. This is relevant to BACII Two different thrombin materials were used in the study. The first one denoted as "Thrombin" is supplied by Omrix Biopharmaceuticals Ltd. Thrombin comprises 1000 IU/ml of thrombin, 6 mg/ml calcium chloride and 6 mg/ml albumin and for the purpose of this study, the solution was diluted by a factor of about 4 (1:4) with either albumin-based buffer solution or albumin-free buffer solution to obtain final solution as detailed in Table 1.

Table 3 detail the components of the albumin-based buffer solution and the albumin-free buffer solution that were used for dilution of thrombin, respectively.

TABLE 3

Thrombin albumin-based and albumin-free buffer solutions*

| Reagent | albumin-based Thrombin buffer Concentration | albumin-free Thrombin buffer |
|---|---|---|
| Sodium Acetate trihydrate | 20 mM | 20 mM |
| D-Mannitol | 0.1M | 0.1M |
| Calcium chloride dihydrate | 40 mM | 40 mM |
| Human Albumin | 0.6% | |
| Sodium Chloride | ~90 mM | ~90 mM |
| pH | 6.8-7.2 | 6.8-7.2 |

*Instead of Albumin water for injection (WFI) was added.

The second source of thrombin denoted herein as "TH04" comprises 100-300 IU/ml of thrombin. TH04 is process fraction in the thrombin manufacture in which thrombin source is free of albumin and calcium ions.

In order to prepare formulations without calcium ion (W/O calcium), 5 mM EDTA that is calcium chelator agent was added.

Example 1A

Ambient Conditions

The % water retention was evaluated one to two hours after the hydrogel formation (hydrogel formation was determined by a visual inspection) under ambient conditions. After one and up to two hours following hydrogel formation the 1 ml hydrogel was subjected to a mild centrifugation of 630 g, having a surface area of about 1 cm² for 30 min inside a centricon tube and the amount of retained water in the hydrogel was assessed. Table 4 summarizes the results of the water retention capacity of the different clots.

TABLE 4 water retention in the various clots

| Exp. No. | % water retained |
|---|---|
| 1 | 56.11 |
| 2 | 37.40 |
| 3 | 58.05 |
| 4 | 48.33 |
| 5 | 54.15 |
| 6 | 45.38 |
| 7 | 42.52 |
| 8 | 37.65 |
| 9 | 61.59 |
| 10 | 47.58 |
| 11 | 59.99 |
| 12 | 52.18 |

Example 1B

High Pressure

The % water retention of hydrogels was evaluated shortly after hydrogel formation (hydrogel formation was determined by a visual inspection) under high pressure conditions. Following hydrogel formation, the 1 ml hydrogel was subjected to a centrifugation in an Eppendorf tube 0.7-1 cm² at 31,514 g (a pressure of about 457 PSI) for 30 mins and the amount of retained water in the hydrogel was assessed. Table 5 summarizes the results of the water retention capacity of the different hydrogels.

TABLE 5 water retention in the various clots

| Exp. No. | Dilution of fibrin-ogen | Albumin conc in the total solution mg/ml | free calcium ions are present | % retained from initial weight after 1st centrifugation | % lost from initial weight after 1st centrifugation |
|---|---|---|---|---|---|
| 1 | 1:4 | 48.20 | + | 57.55 | 42.45 |
| 2 | 1:8 | 52.20 | + | 29.32 | 70.68 |
| 3 | 1:4 | 1.8 | + | 89.66 | 10.34 |
| 4 | 1:8 | 1.25 | + | 88.52 | 11.48 |
| 5 | 1:4 | 48.20 | − | 64.35 | 35.65 |
| 6 | 1:8 | 52.50 | − | 23.55 | 76.45 |
| 7 | 1:4 | 1.80 | − | 91.19 | 8.81 |
| 8 | 1:8 | 1.25 | − | 87.97 | 12.03 |
| 9 | 1:4 | 45.20 | − | 26.87 | 73.13 |
| 10 | 1:8 | 49.50 | − | 6.92 | 93.08 |
| 11 | 1:4 | 1.20 | − | 70.46 | 29.54 |
| 12 | 1:8 | 0.67 | − | 16.89 | 83.11 |

The results show that the clots (formed with fibrinogen diluted both 1:4 and 1:8, having a concentration of fibrinogen 14 mg/ml and 8 mg/ml, respectively and thrombin at a ratio of 1:1) fibrinogen in the 1:1 mix (7 mg/ml and 4 mg/ml) is 70 or 73% of the total protein (total protein in the mix 10 and 5.5 mg/ml, respectively) enable to retain the higher amount of water when albumin is higher than 0.67 mg/ml (12% of total protein) or equal or higher than 1.2 mg/ml (12% of total protein) and up to equal to 1.8 mg/ml (18% of total protein).

The results further show that the hydrogel or clots (formed with fibrinogen diluted both 1:4 and 1:8, having a concentration of fibrinogen 14 mg/ml and 8 mg/ml and diluted 1:1 with thrombin) fibrinogen is 70 or 73% of the total protein enable to retain the highest amount of water when albumin is equal than 1.25 mg/ml (6.5% of total protein) and up to equal to 1.8 mg/ml (18% of total protein (Exp 3)).

The results further show the importance of low amounts of albumin's presence (e.g. lower than 45.2 mg/ml, e.g. 1.2, 1.25, 1.8 mg/ml) in hydrogels prepared with low concentration of fibrinogen e.g. having a concentration of fibrinogen in the mixture (thrombin: fibrinogen 1:1) of less than about 7 mg/ml e.g. 3.9 mg/ml.

The results also show that the presence of EDTA (Ethylenediaminetetraacetic acid) or in the absence of free calcium, did not change the clot capability to retain the water, i.e. the trend of the water loss was the same like in Groups 1-4 (with the presence of free calcium).

Example 3

The Effect of Fibrinogen and Albumin in a Rabbit Uterine Horn Model

The purpose of this study was to characterize the efficacy of various formulations with different concentrations of fibrinogen and albumin in a rabbit uterine horn adhesion model.

Materials and Methods:
The Test System

Juvenile/young adult (13-15 weeks old at surgery) female New Zealand white rabbits (*Oryctolagus cuniculus*) were used in the study. Rabbits were obtained from Western Oregon Rabbit Co., PO Box 653, Philomath, OR USA and were individually identified by unique, ear tags, applied by the supplier.

Animals were examined by experienced animal care personnel shortly after arrival at the test facility.

Animals were acclimated for a minimum of 5 days prior to initiation of the study and monitored by experienced animal care personnel daily. Animals supplied for this study were used only if they appeared grossly normal (i.e., showing a clean unruffled coat, bright clear eyes, no unusual exudate from body orifices, alert and active posture).

Environment and Husbandry:

Animals were individually housed in stainless steel cages, each labeled with an individual card indicating the study number and the individual animal number. The room environment was maintained at approximately 68° F. (approximately 20° C.) with 30-70% relative humidity and a light/dark cycle of 12 hours/12 hours.

Purina Prolab Rabbit diet 15% protein (LabDiet, St. Louis, MO) and tap water was provided ad libitum to the animals for the duration of the study and carrots and alfalfa cubes.

Pre-Operative Preparation Adhesion was studied using surgery. Animals were weighed on the day of surgery. Anesthesia was induced and maintained by inhalation of isoflurane (5% and 3.5% concentration, respectively). Depilation of the surgical site was accomplished with an electric animal clipper. The area was vacuumed to remove hair clippings and debris, and then rinsed with isopropyl alcohol 70%. The bladder was expressed (i.e. manipulated externally to force urine out of it). The entire area was painted with an aqueous iodophor solution (iodine scrub) of 1% available iodine. The area was then swabbed with 70% isopropyl alcohol solution.

Procedures were performed in a sterile manner in a room reserved for aseptic survival surgery. Sterile towels, drapes, and instruments were used. The anesthetized and surgically prepared rabbit was delivered to the operating table and restrained via the limbs in the desired recumbent position. A sterile incise drape was applied to the prepared area. Since there is an approximate correlation between animal weight and uterine horn size, in order to avoid operating on animals with smaller or larger out-of-range horns, and since there were two consecutive surgery days in each of two consecutive weeks, animals were assigned to surgery in a sequential order based on their weight. The assignment of an animal to one of the study groups was made according to its sequential surgery assignment.

Justification of the Test System:

The rabbit uterine horn simple abrasion model is performed essentially as described in Wiseman 1992, (Effect of thrombin induced hemostasis on the efficacy of an absorbable adhesion barrier. The journal of reproductive medicine vol 37 No 9, September 1992).

Six animals per group are to be entered into the study. Given the variances observed historically, these group sizes are sufficient to provide the study with sufficient power to detect statistical differences between treatment and control group. This model has been used extensively for the determination of efficacy of putative anti-adhesion agents, and good correlations exist between data obtained in animals and that obtained clinically (Wiseman, 1999 Effect of different barriers of oxidized regenerated cellulose (ORC) on cecal and sidewall adhesions in the presence and absence of bleeding. Journal of Investigative Surgery 12:141-146).

The 42 sequentially assigned animals were randomized by lottery by a disinterested individual in blocks of 7 so that each of the study groups was represented in each block.

The rabbit uterine horn simple abrasion model was conducted as described by Wiseman et al., 1992.

Intra-Operative Procedure: The abdomen was entered via a midline laparotomy incision about 6 cm long. The bladder and uterus were delivered into the wound.

Only those animals with two uterine horns with a diameter of between 9 and 16 French, inclusive, were entered into the study. Using a number 10 scalpel blade, 5 cm lengths of uterine horn, approximately 1 cm from the uterine bifurcation, were scraped, 40 times per side. Hemostasis was controlled by tamponade with gauze. If necessary small vessels were ligated. Organs were repositioned anatomically. During the treatment, the animals were observed carefully to remove any animal with unexpected response to the anesthetic treatment. Controls consisted of animals in which all surgical procedures have been performed, but without the application of test materials.

Tested formulas were used in vials of 5 ml of each component per animal were thawed at room temperature before induction of anesthesia. Each product was handled according to the manufacturer's instructions and delivered by spraying using the Omrix application airless spray device. Enough product was applied so as to cover the traumatised surfaces with a thin film. The volume applied was recorded.

Post-Operative Procedure Abdominal incisions were closed using a continuous Vicryl 4-0 suture. Fascia was closed loosely with 4-0 Vicryl and the skin closed with undyed 4-0 Vicryl (cutting needle) using a subcuticular suturing method. Three doses of buprenorphine (Buprenex) (0.03 mg/kg, 0.4 ml×0.3 mg/ml) were given by subcutaneous injection, one on the morning of surgery, one six to eight hours later and one the following morning. Further doses were given if deemed necessary by the veterinarian.

Clinical Signs of Animals: All animals were observed closely until vertical recumbency was resumed, when they were returned to their cages. Rabbits were placed under a heat lamp or on a heating blanket for this initial post-operative period.

Each rabbit was observed daily after surgery to determine its health status on the basis of general attitude and appearance, food consumption, weight loss, fecal and urinary excretion and presence of abnormal discharges. Animals were observed daily for incisional integrity, excessive bruising and infection, evaluation of pain and/or discomfort and were given analgesics additional to the standard doses described above. Animals were euthanized if deemed necessary by the attending veterinarian and excluded from analysis.

Daily monitoring records were kept. Unusual findings were reported to the study director and/or the veterinarian and a decision made to treat an animal or, in the case of a moribund animal, to euthanize it. Moribund animals were euthanized and recorded.

Animal husbandry personnel were blinded as to the group assignment.

Adhesion and Tenacity Detection: Adhesion evaluation was done 11-16 days following surgery, animals were euthanized by intravenous injection of 1.5 ml of Beuthanasia-D (sodium pentobarbital 390 mg/ml; phenytoin sodium 50 mg/ml) (Merck Animal Health, Madison, NJ). Body weights of the animals were recorded. The abdomen was opened, and the surgical site inspected. Adhesions were graded by a blinded observer.

Examinations Performed

Extent and Incidence of Adhesions: The length of each uterine horn with adhesions is estimated. Results are expressed as incidence of adhesions (number of uterine horns with adhesions/total number) and extent of adhesions (% length of uterine horn with adhesions).

Tenacity of Adhesions: Tenacity (Severity) of Adhesions (Grade) is graded as 0 (absent), 1 (filmy adhesions), and 2 (tenacious, requiring sharp dissection).

Degree of Uterine Convolution: The degree of uterine convolution, a measure of the anatomical distortion of the organ due to adhesions, is recorded according to the following scale:

No convolution: straight lengths of adherent or nonadherent horns that are clearly seen;

Partly convoluted: horns have adhesions and 50%-75% of the horn length is entangled preventing discernment of the straight portions;

Completely convoluted: it is impossible to see the uterine anatomy because the horn is completely entangled.

Data Analysis of Adhesions: For each animal, the average extent of adhesions is calculated for the two horns. This average is used to calculate the mean extent (percent of the length of the uterus involved) of adhesions (±SEM) for the group, displayed to one decimal place. Comparisons of all groups with the Control group (no treatment) are made using Dunnett's test (Dunnett, 1964). The incidence of adhesions of each group is compared with controls using Fisher's Exact Test, and the tenacity and degree of uterine convolution is compared using the $chi^2$ test. For all tests, the level of statistical significance is taken as $p<0.05$.

Exclusion from Analysis: Upon examination of an animal at necropsy, but before inspection of the surgical site and evaluation of adhesions, a determination is made as to whether the animal should be excluded from the primary analysis. Animals are to be excluded from the primary analysis if there are signs of unusual occurrences that may affect the outcome. Such signs commonly include presence of infection within the abdominal cavity, or excessive weight loss (>10% of body weight). Any decision to exclude an animal is made without knowledge of the group assignment or of the presence or extent of adhesions.

Table 6 below summarizes the experimental details, and Table 7 below presents the results summary for the assessment of the effect of fibrin-based formulations on adhesion formation.

TABLE 6 experimental details

| Exp. No. | Total protein (mg/ml) in Thr/BAC2 1:1 | Fibrinogen (mg/ml) in Thr/BAC2 1:1 | Total albumin (mg/ml) in Thr/BAC2 1:1 | Fibrinogen % from total protein in Thr/BAC2 1:1 | Total protein (mg/ml) | Albumin (Alb) mg/ml In BAC2 (mg/ml) | Alb in Thr (mg/ml) | Fibrinogen component (mg/ml) | Source of fibrinogen and buffer | Thrombin component Thrombin (IU/ml) and Source of thrombin buffer |
|---|---|---|---|---|---|---|---|---|---|---|
| 1 | 45.5 | 11.5 | 42 | 25% | 91 | 77 | 6 | 23 | BAC2 (1:2) W/albumin | 161 W/albumin |
| 2 | 47 | 4.5 | 50 | 9.5% | 94 | 94 | 6 | 9 | BAC2 (1:6) W/albumin | 161 W/albumin |
| 3 | 18 | 11.5 | 3 | 67% | 36 | 4 | 2 | 23 | BAC2 (1:2) W/O albumin | 153 W/O albumin |
| 4 | 10 | 5.5 | 1.5 | 55% | 20 | 2 | 1 | 11 | BAC2 (1:6) W/O albumin | 153 W/O albumin |
| 5 | 55 | 7 | 58 | 13.7% | 102 | 110 | 6 | 14 | pure fibrinogen W/albumin | 161 W/albumin |
| 6 | 55 | 8.5 | 58 | 21.25% | 80 | 110 | 6 | 17 | pure fibrinogen W/albumin | 161 W/albumin |

TABLE 7

Results summary for the assessment of the effect of fibrin-based formulations on adhesion formation

| Exp. No. | Extent (Adhesion) %[1] | p[2] | Adhesion Free[3] | Grade[4] | P# | Conv[5] | p# |
|---|---|---|---|---|---|---|---|
| control | 67 | NA | 0 | 0/1/11 | | 3/5/4 | |
| 1 | 32 | 0.039 | 6.3 | 1/5/10 | | 12/4/0 | 0.012 |
| 2 | 33 | 0.047 | 0 | 0/5/7 | | 10/2/0 | 0.012 |
| 3 | 18 | 0.008* | 21.4 | 3/5/6 | 0.034 | 14/0/0 | 0.0004 |
| 4 | 32 | 0.07 | 8.3 | 1/7/4 | 0.013 | 10/0/2 | 0.01 |
| 5 | 33 | 0.07 | 7.1 | 1/6/7 | 0.078 | 8/4/2 | |
| 6 | 59 | 0.67 | 7.1 | 1/4/9 | | 9/1/4 | 0.063 |

[1] % of length of uterine horn with adhesions, mean of left and right horns
[2] p value for Student's t- test against Control
[3] % of uterine horns free of adhesions (number of uterine horns free of adhesions/total)
[4] Number of horns with no adhesions/grade 1 adhesions/ grade 2 adhesions
[5] Number of horns with no convolution/partial convolution/full convolution
*p < 0.05 Dunnett's t test vs. Control
p value χ 2 test, vs Control). Only values <0.1 shown.

An improved anti-adhesion activity was observed in Exp. 3 indicating that the kit described herein has a superior anti-adhesion activity.

Table 8 and 9 present a summary of discrete data statistic for 6-8 samples used for the anti-adhesion experiments tested for each composition (fibrinogen component-Table 8; and fibrinogen and thrombin in Table 9).

TABLE 8

Summary of discrete data statistic for 6-8 samples used for the anti-adhesion experiments tested for each composition (fibrinogen component)

| Threshold set to above 35% | Control | #1 (mg/ml) *FGBAC2 23 + total protein 91 + Alb 77 | #2 (mg/ml) FGBAC2 9 + total protein 94 + Alb aprox. 94 | #3 (mg/ml) FGBAC2 23 + Total protein 36 + Alb 4 | #4 (mg/ml) FGBAC2 11 + total protein 20 + Alb 2 | #5 (mg/ml) **FGPure Fibrinogen 14 + total protein 102 + Alb. Aprox. 110 | #6 (mg/ml) FG Pure Fibrinogen 17 + total protein 80 + alb. aprox approx. 110 |
|---|---|---|---|---|---|---|---|
| Extent *** | 70.0 | 45.0 | 35.0 | 0.0 | 35.0 | 75.0 | 42.5 |
| Extent *** | 90.0 | 40.0 | 41.5 | 25.0 | 8.0 | 15.0 | 100.0 |
| Extent *** | 60.0 | 33.5 | 60.0 | 26.5 | 16.5 | 11.0 | 7.5 |
| Extent *** | 10.5 | 65.0 | 8.0 | 35.0 | 85.0 | 11.0 | 45.0 |
| Extent *** | 92.5 | 10.0 | 35.0 | 2.5 | 15.0 | 5.0 | 90.0 |
| Extent *** | 77.5 | 16.0 | 20.0 | 20.0 | 35.0 | 80.0 | 25.0 |
| Extent *** |  | 4.0 |  | 17.0 |  | 33.0 | 100.0 |
| Extent *** |  | 41.5 |  |  |  |  |  |
| Average Extent *** | 67 | 32 | 33 | 18 | 32 | 33 | 59 |
| individual results above the threshold | 5 | 4 | 2 | 0 | 1 | 2 | 5 |
| Overall No. of results per group | 6 | 8 | 6 | 7 | 6 | 7 | 7 |
| Proportion of results above threshold | 0.83 | 0.50 | 0.33 | 0.00 | 0.17 | 0.29 | 0.71 |

*FGBACII = fibrinogen in BACII
**FGPure Fibrinogen = Fibrinogen in Pure fibrinogen;
*** % adhesion

TABLE 9

Summary of discrete data statistic for 6-8 samples for the anti-adhesion experiments tested for each composition (fibrinogen and thrombin)

| Threshold set to above 35% | Control | #1 (mg/ml) FGBAC2 11.5 + total protein 45.5 + Alb 42 | #2 (mg/ml) FGBAC2 4.5 + total protein 47 + Alb approx. 50 | #3 (mg/ml) FGBAC2 11.5 + total protein 18 + Alb 3 | #4 (mg/ml) FGBAC2 5.5 + total protein 10 + Alb 1.5 | #5 (mg/ml) FGPure fibrinogen 7 + total protein 54 + Alb aprox. 58 | #6 (mg/ml) FGPure fibrinogen 8.5 + total protein 43 + Alb approx. 58 |
|---|---|---|---|---|---|---|---|
| Extent* | 70.0 | 45.0 | 35.0 | 0.0 | 35.0 | 75.0 | 42.5 |
| Extent* | 90.0 | 40.0 | 41.5 | 25.0 | 8.0 | 15.0 | 100.0 |
| Extent* | 60.0 | 33.5 | 60.0 | 26.5 | 16.5 | 11.0 | 7.5 |
| Extent* | 10.5 | 65.0 | 8.0 | 35.0 | 85.0 | 11.0 | 45.0 |
| Extent* | 92.5 | 10.0 | 35.0 | 2.5 | 15.0 | 5.0 | 90.0 |
| Extent* | 77.5 | 16.0 | 20.0 | 20.0 | 35.0 | 80.0 | 25.0 |
| Extent* |  | 4.0 |  | 17.0 |  | 33.0 | 100.0 |
| Extent * |  | 41.5 |  |  |  |  |  |
| Average Extent* | 67 | 32 | 33 | 18 | 32 | 33 | 59 |
| individual results above the threshold | 5 | 4 | 2 | 0 | 1 | 2 | 5 |

TABLE 9-continued

Summary of discrete data statistic for 6-8 samples for the anti-adhesion experiments tested for each composition (fibrinogen and thrombin)

| Threshold set to above 35% | Control | #1 (mg/ml) FGBAC2 11.5 + total protein 45.5 + Alb 42 | #2 (mg/ml) FGBAC2 4.5 + total protein 47 + Alb approx. 50 | #3 (mg/ml) FGBAC2 11.5 + total protein 18 + Alb 3 | #4 (mg/ml) FGBAC2 5.5 + total protein 10 + Alb 1.5 | #5 (mg/ml) FGPure fibrinogen 7 + total protein 54 + Alb aprox. 58 | #6 (mg/ml) FGPure fibrinogen 8.5 + total protein 43 + Alb approx. 58 |
|---|---|---|---|---|---|---|---|
| Overall No. of results per group | 6 | 8 | 6 | 7 | 6 | 7 | 7 |
| Proportion of results above threshold | 0.83 | 0.50 | 0.33 | 0.00 | 0.17 | 0.29 | 0.71 |

**% adhesion

The most effective adhesion prevention was obtained with samples 3 and 4. The total protein in samples 3 and 4 is about 18 and 10 mg/ml, fibrinogen is 67% and 55% out of the total protein, and albumin 3 mg/ml (16.7% out of the total protein) and 1.5 mg/ml (15% out of the total protein), respectively.

The comparative statistical analysis further confirms that with the adhesion extent threshold being set as above 35% the best anti-adhesion activity was observed in Exp. 3, showing no sample above the threshold.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

The invention claimed is:

1. A kit comprising:
   (i) a first container comprising a solution of plasma cryoprecipitate-containing component comprising fibrinogen at a concentration range of about 10 mg/ml to about 25 mg/ml and having a total protein concentration range of about 15 mg/ml to about 40 mg/ml, wherein the fibrinogen is in a range of about 50% to less than 80% of total protein by weight, wherein the cryoprecipitate is depleted from plasmin and/or plasminogen, does not comprise tranexamic acid or aprotinin, and comprises factor XIII, fibronectin and optionally one or more members selected from factor VIII, von Willebrand factor (vWF), and vitronectin; and
   (ii) a second container comprising a solution of thrombin-containing component;
   wherein: the cryoprecipitate-containing component comprises albumin at a concentration ranging from 1.2 mg/ml up to about 3 mg/ml; and wherein the cryoprecipitate-containing component and/or the thrombin-containing component comprise free calcium ions.

2. The kit of claim 1, wherein the cryoprecipitate-containing component comprises total protein at a concentration range between about 20 mg/ml to about 40 mg/ml.

3. The kit of claim 1, wherein the thrombin-containing component comprises thrombin at a concentration range of between about 100 IU/ml to about 300 IU/ml.

4. The kit of claim 1, wherein the cryoprecipitate is a biologically active component of a plasma cryoprecipitate-derived from antihaemophilic factor preparation.

5. The kit of claim 1, wherein the cryoprecipitate-containing component and/or the thrombin-containing component are in a liquid or frozen form.

6. The kit of claim 1, for use in producing an anti-adhesive mixture, optionally for use in preventing/reducing tissue adhesion following an invasive procedure, and optionally wherein the invasive procedure is a surgical procedure or a diagnostic procedure.

7. The kit of claim 1, wherein the first container and/or the second container are an applicator, optionally wherein the applicator is a syringe, optionally the kit being administered by spraying or dripping the solutions onto a tissue.

8. A two-component mixture comprising (i) a plasma cryoprecipitate comprising: fibrinogen, and albumin in a range of 1.2 mg/ml to 3 mg/ml and (ii) thrombin; wherein the mixture comprises free calcium ions, total protein in a range of about 2.5 mg/ml to about 30 mg/ml, fibrinogen in a range of about 50% to less than 80% of total protein by weight; and wherein the plasma cryoprecipitate being depleted from plasmin and/or plasminogen, does not comprise tranexamic acid or aprotinin, and comprises factor XIII, fibronectin, and optionally one or more members selected from factor VIII, von Willebrand factor (vWF), and vitronectin.

9. A two-component composition for use in preventing tissue adhesion, comprising:
   component A comprising: a plasma cryoprecipitate-containing solution comprising fibrinogen at a concentration range of about 10 mg/ml to about 25 mg/ml, and a total protein concentration range of about 15 mg/ml to about 40 mg/ml, wherein the fibrinogen is in a range of about 50% to less than 80% of total protein by weight; and component B comprising thrombin; wherein:
   component A comprises albumin at a concentration ranging from 1.2 mg/ml up to about 1.53 mg/ml; wherein component A and/or component B comprises free calcium ions, and wherein the cryoprecipitate is depleted from plasmin and/or plasminogen, does not comprise tranexamic acid or aprotinin, and comprises factor XIII, fibronectin, and optionally one or more members selected from factor VIII, von Willebrand factor (vWF), and vitronectin.

10. The two-component composition of claim 9, wherein the total protein concentration is in a range of about 20 mg/ml to about 40 mg/ml.

11. The two-component composition of claim 9, wherein component B comprises thrombin at a concentration range of between about 100 IU/ml to about 300 IU/ml.

\* \* \* \* \*